(12) United States Patent
Sofranko

(10) Patent No.: US 10,919,027 B1
(45) Date of Patent: Feb. 16, 2021

(54) STABILIZED OXYBORATES AND THEIR USE FOR OXIDATIVE CONVERSION OF HYDROCARBONS

(71) Applicant: Bio2Electric, LLC, Woburn, MA (US)

(72) Inventor: John A. Sofranko, Weston, MA (US)

(73) Assignee: EcoCatalytic Inc., Woburn, MA (US)

( * ) Notice: Subject to any disclaimer, the term of this patent is extended or adjusted under 35 U.S.C. 154(b) by 0 days.

(21) Appl. No.: 16/845,815

(22) Filed: Apr. 10, 2020

Related U.S. Application Data

(60) Provisional application No. 62/835,053, filed on Apr. 17, 2019.

(51) Int. Cl.
*B01J 23/78* (2006.01)
*C07C 5/48* (2006.01)
*B01J 27/18* (2006.01)
*B01J 21/02* (2006.01)

(52) U.S. Cl.
CPC ........... *B01J 23/78* (2013.01); *B01J 27/1806* (2013.01); *C07C 5/48* (2013.01); *B01J 21/02* (2013.01)

(58) Field of Classification Search
None
See application file for complete search history.

(56) References Cited

U.S. PATENT DOCUMENTS

| | | | |
|---|---|---|---|
| 2,493,038 A | 1/1950 | Snyder et al. | |
| 3,651,121 A * | 3/1972 | Duke et al. | C07C 1/20 558/382 |
| 4,544,785 A | 10/1985 | Withers et al. | |
| 4,547,607 A | 10/1985 | Jones et al. | |
| 4,599,477 A | 7/1986 | Robinson et al. | |
| 4,670,619 A | 6/1987 | Withers, Jr. et al. | |
| 4,777,313 A | 10/1988 | Sofranko et al. | |

(Continued)

FOREIGN PATENT DOCUMENTS

EP 2576046 B1 11/2014
EP 2853521 A1 4/2015
(Continued)

OTHER PUBLICATIONS

Xu, Longya, et al. "Combination of CH4 oxidative coupling reaction with C2H6 oxidative dehydrogenation by CO2 to C2H4". Fuel 81. 1593-1597.*

(Continued)

*Primary Examiner* — Sheng H Davis
(74) *Attorney, Agent, or Firm* — RatnerPrestia

(57) ABSTRACT

An oxygen transfer agent comprising a metal-boron oxide is provided. The average oxidation state of the metal in the metal-boron oxide is about 3+, and has 10% or less of a stoichiometric excess in moles of Mn with respect to the boron. The oxygen transfer agent may further comprise a magnesia-phosphate cement. The oxygen transfer agent is capable of oxidatively dehydrogenating a hydrocarbon feed at reaction conditions to produce a dehydrogenated hydrocarbon product and water. The oxidative dehydrogenation can take place under reaction conditions of less than 1000 ppm weight molecular oxygen, or in the presence of more than 1000 ppm weight of molecular oxygen. Also provided are methods of using the oxygen transfer agents, and an apparatus for effecting the oxidative dehydrogenation of the hydrocarbon feed.

27 Claims, 3 Drawing Sheets

(56) References Cited

U.S. PATENT DOCUMENTS

| | | | |
|---|---|---|---|
| 4,830,728 A | 5/1989 | Herbst et al. | |
| 5,026,947 A * | 6/1991 | Mazurek | C07C 2/84 585/500 |
| 5,079,385 A | 1/1992 | Wu | |
| 5,091,163 A | 2/1992 | Gaffney et al. | |
| 5,192,809 A | 3/1993 | Jones et al. | |
| 5,545,787 A | 8/1996 | Cooper et al. | |
| 6,403,523 B1 * | 6/2002 | Cantrell | B01J 27/232 502/174 |
| 9,963,407 B2 | 5/2018 | Stine et al. | |
| 10,138,182 B2 | 11/2018 | Sofranko et al. | |
| 10,550,051 B2 | 2/2020 | Li et al. | |
| 2003/0181325 A1 | 9/2003 | Ou et al. | |
| 2005/0124841 A1 | 6/2005 | Rapier et al. | |
| 2011/0245571 A1 * | 10/2011 | Kustov | B01J 27/0576 585/658 |
| 2012/0041246 A1 | 2/2012 | Scher et al. | |
| 2012/0203042 A1 | 8/2012 | Huber et al. | |
| 2014/0275667 A1 | 9/2014 | Sarker | |
| 2014/0371504 A1 | 12/2014 | Stine et al. | |
| 2017/0226030 A1 | 8/2017 | Li et al. | |
| 2019/0022626 A1 * | 1/2019 | Schammel | C07C 2/84 |
| 2019/0315667 A1 | 10/2019 | Sofranko et al. | |

FOREIGN PATENT DOCUMENTS

| | | |
|---|---|---|
| WO | 2014202501 * | 12/2014 |
| WO | 2018005456 A1 | 1/2018 |
| WO | 2018049389 A1 | 3/2018 |
| WO | 2018157042 A1 | 8/2018 |
| WO | 2018232133 A1 | 12/2018 |

OTHER PUBLICATIONS

Guo et al., "Recent Advances in $CaSO_4$ Oxygen Carrier for Chemical-Looping Combustion (CLC) Process", Chemical Engineering Communications, 2012, vol. 199, No. 11, pp. 1463-1491.

Anene et al., "Experimental Study of Thermal and Catalytic Pyrolysis of Plastic Waste Components", Sustainability, 2018, vol. 10, 3979.

Carey, J., "On the Brink of a Recycling Revolution?", PNAS, Jan. 24, 2017, vol. 114, No. 4, pp. 612-616.

Currao et al., "Understanding Zeolite Frameworks", Department of Chemistry and Biochemistry, University of Bern, 65 pages.

Elbadawi et al., "Kinetics of oxidative cracking of n-hexane to olefins over VO2/Ce—Al2—O3 under gas phase oxygen-free environment", http://onlinelibrary.wiley.com/doi/10.1002/aic.15491/abstract, 2 pages.

Lemonick, S., "Chemistry may have solutions to our plastic trash problem", Pollution, 2018, vol. 96, Iss. 25, 9 pages.

Olazar et al, "Light Olefins From HDPE Cracking in a Two-Step Thermal and Catalytic Process", Chemical Engineering Journal, 2012, 207-208 pp. 27-34.

World Economic Forum, Ellen MacArthur Foundation, "The New Plastics Economy—Rethinking the Future of Plastics", http://ellenmacarthurfoundation.org/publications/the-new-plastics-economy-rethinking-the-future-of-plastics, 120 pages.

Baerlocher, "Atlas of Zeolite Framework Types," Fifth Revised Edition, 2001, 40 pages.

Baerlocher, et al., "Atlas of Zeolite Framework Types," Sixth Revised Edition, 2007, 404 pages.

Boyadjian, C. et al., Catalytic o\Oxidative Cracking of Hexane as a Route to Olefins, Applied Catalysis A: General, 2010, vol. 372, pp. 167-174.

Breck, D.W., General Introduction, Chapter 1, Zeolite Molecular Sieves: Structure, Chemistry, and Use, Wiley, 1974, 28 pages.

Davis, B., "Identification of Molecular Sieve Structures," 1989, pp. 282-347, Van Nostrand Reinhold Catalysis Series.

Fumoto, E., et al., "Production of Light Oil by Oxidative Cracking of Oil Sand Bitumen Using Iron Oxide Catalysts in a Steam Atmosphere," Energy Fuels, 2011, vol. 25, pp. 524-527.

Garcia, J.M., et al., "The Future of Plastics Recycling," Science, Nov. 17, 2017, vol. 358, Issue 6325, pp. 870-872.

Ishihara, Y., et al., "Mechanism for Gas Formation in Polyethylene Catalytic Decomposition," Polymer, 1992, vol. 33, No. 16, pp. 3482-3486.

Karge, et al., Post-Synthesis Modification I (Molecular Sieves), 2002, vol. 1, pp. 1-54.

Lee, H.W., et al., "Catalytic Pyrolysis of Polyethylene and Polypropylene Over Desilicated Beta and A1-MSU-F," Catalysts, 2018, vol. 8, No. 501, pp. 1-15.

Manos, G., et al., "Catalytic Degradation of High-Density Polyethylene on an Ultrastable-Y Zeolite. Nature of Initial Polymer Reactions, Pattern of Formation of Gas and Liquid Products, and Temperature Effects," Industrial & Engineering Chemistry Research, Mar. 25, 2000, vol. 39, No. 5, pp. 1203-1208.

Wu, E.L. et al., "Hydrocarbon Adsorption Characterization of Some High Silica Zeolites," pp. 547-554.

Marcilla, A., et al., "Study of the Catalytic Pyrolysis Behavior of Polyethylene-Polypropylene Mixtures," Journal of Analytical and Applied Pyrolysis, 2005, vol. 74, pp. 387-392.

Rahimi, A., et al., "Chemical Recycling of Waste Plastics for New Materials Production," Nature Reviews—Chemistry, Jun. 17, 2017, vol. 1, Article 0046, pp. 1-11.

Seo, Y-H., et al., "Investigation of Catalytic Degradation of High-Density Polyethylene by Hydrocarbon Group Type Analysis," Journal of Analytical and Applied Pyrolysis, 2003, vol. 70, pp. 383-398.

Szostak, R., Molecular Sieves—Principles of Synthesis and Identification, 17 pages, Van Nostrand Reinhold Catalysis Series.

Weitkamp, J., et al.,"Preparation of Oxide, Sulfide and Other Chalcogenide Clusters in Molecular Sieves," Molecular Sieves, 2002, vol. 3, pp. 339-414.

Sofranko et al., "Natural Gas to Gasoline: the ARCO GTG Process", Symposium on Methane Activation, Conversion and Utilization, International Congress of Pacific Basin Societes, Dec. 17-20, 1989, pp. 152.154.

Non Final Office Action for U.S. Appl. No. 16/800,883, dated Jun. 15, 2020, 30 pages.

Jordi Labs, "Typical Molecular Weights of Common Polymers", 2020 downloaded from https://jordilabs.com/blog/typical-polymer-molecular-weights, 5 pages.

Bovin et al., Electron Microscopy of Oxyborates. I. Defect Structures in the Minerals Pinakiolite, Ludwigite, Orthopinakiolite and Takéuchiite, Acta Cryst., 1981, vol. A37, pp. 28-35.

Kasper et al., "A New Structure Type for Metallic Oxides of Formula $A_6BO_8$", J. Chem. Phys, 1953, vol. 21, pp. 1897-1898.

Sofronova et al., "Ludwigites: From Natural Mineral to Modern Solid Solutions", Cryst. Res. Technol, 2017, vol. 52, No. 4, 19 pages.

De Vries et al., "The Thermal Decomposition of Potassium and Sodium-Pyrosulfate", J. Inorg. Nucl. Chem., 1968, vol. 31, pp. 1307-1313.

Neal et al., "Oxidative Dehydrogenation of Ethane: A Chemical Looping Approach", Energy Technology, 2016, vol. 4, pp. 1-10.

Sofranko et al., "The Oxidative Conversion of Methane to Higher Hydrocarbons", Journal of Catalysis, 1987, vol. 103, pp. 302-310.

Non Final Office Action for U.S. Appl. No. 16/888,066, dated Aug. 14, 2020, 27 pages.

Non Final Office Action for U.S. Appl. No. 16/877,992, dated Aug. 7, 2020, 32 pages.

Ding, N. et al., "Effect of hematite addition to $CaSO_4$ oxygen carrier in chemical looping combustion of coal char," Jun. 15, 2015, vol. 5, pp. 56362-56376, RSC Advances, The Royal Society of Chemistry.

Li, H. et al., "Catalytic reduction of calcium sulfate to calcium sulfide by carbon monoxide," Aug. 3, 1999, vol. 38, pp. 3333-3337, Industrial & Engineering Chemistry Research.

Xiao, J. "The diffusion mechanism of hydrocarbons in zeolites," Thesis, Massachusetts Institute of Technology, Jun. 8, 1990, 195 pages.

* cited by examiner

STABILIZED OXYBORATES AND THEIR USE FOR OXIDATIVE CONVERSION OF HYDROCARBONS

CROSS REFERENCE TO RELATED APPLICATIONS

This application claims the benefit of and priority from U.S. Provisional Application No. 62/835,053, filed on Apr. 17, 2019, the disclosure of which is incorporated by reference herein in its entirety for all purposes.

TECHNICAL FIELD

The present disclosure relates to oxidative coupling of methane (OCM) and the oxidative dehydrogenation (ODH) of ethane and higher hydrocarbons.

BACKGROUND

Oxidative coupling of methane (OCM) and oxidative dehydrogenation (ODH) of ethane and higher hydrocarbons are reactions of significant commercial value. These conversions may be done either catalytically by feeding a hydrocarbon and an oxygen containing gas, or in a redox oxygen transfer mode whereby an oxygen transfer agent (OTA) supplies the necessary oxygen for the formation of water. Either system is exemplified by equation (1).

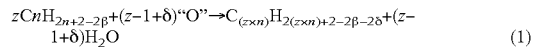

$$zCnH_{2n+2-2\beta}+(z-1+\delta)\text{"O"} \rightarrow C_{(z\times n)}H_{2(z\times n)+2-2\beta-2\delta}+(z-1+\delta)H_2O \quad (1)$$

where: z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen, "O" in equation (1) may be supplied by the reduction of a metal oxide or via the catalytic use of molecular oxygen, i.e., $O_2$. The agent that supplies the oxygen, whether a reducible metal oxide or another type of catalyst, or catalyst system, may be referred to herein as an oxygen transfer agent (OTA).

Since OCM and most ODH reactions are quite exothermic, a preferred reactor system for these transformations are moving or fluid beds. A commercially viable catalyst or oxygen transfer agent (OTA) will not only promote high conversion of the feeds to high selectivities of the desired products, thereby minimizing unwanted COx and coke products, but the catalyst should preferably have the proper physical properties to be used these reactors. These desirable physical properties include:

- an ability to maintain fluidization at reaction temperatures; e.g. not be prone to agglomeration or excessive attrition at high temperature and thus maintain a free flowing mixture of gas and solid at reaction temperature;
- good physical strength and low attrition under fluidization conditions and be able to maintain these properties over many of redox (or chemical looping) cycles;
- an ability to maintain the desired reaction conversion rate and selectivity to the desired products for at least one month;
- an absence of highly toxic materials, or of materials having a geometry that may cause asbestosis;
- suitability for use in in a circulating fluid bed reactor; and
- resistance to deactivation and loss of product selectivity when exposed to common natural gas poisons such as hydrogen sulfide, carbon dioxide, water, and the like.

In addition to these desirable physical properties, the catalyst should preferably also be inexpensive to manufacture on a large scale and comparable in cost to other commercial fluid catalysts such as, for example, fluid catalytic cracking (FCC) catalysts.

There remains a need for such catalyst systems that are selective for both oxidative coupling of methane (OCM) and the oxidative dehydrogenation (ODH) of ethane and higher hydrocarbons, are robust in the challenging conditions in fluidized bed reactors and at the same time are cost-effective to manufacture.

SUMMARY

The inventor has discovered a family of oxyborates that have all of these properties and may be used as an oxygen transfer agent or catalyst for OCM or ODH systems. These materials may have the general empirical formula:

$$M_3BO_5 \quad (2)$$

Or more specifically,

$$M_2'M''BO_5 \quad (3)$$

The oxyborate may further comprise a magnesia-phosphate cement.

An oxygen transfer agent comprising a metal-boron oxide; a magnesia-phosphate cement; and 5% by weight or less of $Mg_6MnO_8$ is provided. The average oxidation state of the metal in the metal-boron oxide is from 2.7+ to less than 4.0+, and the at least one oxygen transfer agent comprises 10% or less of a stoichiometric excess in moles of Mn with respect to the boron in the oxygen transfer agent. The magnesia-phosphate cement comprises: $MgM'''PO_4.mH_2O$, wherein m is an integer from 0 to 6.

A method of oxidatively dehydrogenating a hydrocarbon feed to produce a dehydrogenated hydrocarbon product and water is provided. The method comprises:

a) contacting the hydrocarbon feed with at least one oxygen transfer agent comprising a metal-boron oxide, wherein the average oxidation state of the metal in the metal-boron oxide is from 2.7+ to less than 4.0+, and the at least one oxygen transfer agent comprises 10% or less of a stoichiometric excess in moles of Mn with respect to the boron in the at least one oxygen transfer agent; and b) oxidatively dehydrogenating the hydrocarbon feed at reaction conditions to produce the dehydrogenated hydrocarbon product and the water, and wherein at least a portion of the oxygen transfer agent is reduced to produce a reduced oxygen transfer agent.

An apparatus for producing a dehydrogenated hydrocarbon product by oxidative dehydrogenation of a hydrocarbon feed to produce the dehydrogenated hydrocarbon product and water is provided. The apparatus comprises a vessel configured and arranged for:

i) contacting the hydrocarbon feed with at least one oxygen transfer agent comprising a metal-boron oxide, wherein the average oxidation state of the metal is from 2.7+ to less than 4.0+, and the at least one oxygen transfer agent comprises 10% or less of a stoichiometric excess of Mn with respect to the boron in the oxygen transfer agent; and ii) oxidatively dehydrogenating the hydrocarbon feed at reaction conditions to produce the dehydrogenated hydrocarbon product and the water and to convert a portion of the oxygen transfer agent to a reduced oxygen transfer agent, wherein the reaction conditions comprise reaction conditions comprise less than 1000 ppm weight of molecular oxygen with respect to the total amount of hydrocarbon feed, the oxygen transfer agent and the molecular oxygen.

DETAILED DESCRIPTION OF CERTAIN EMBODIMENTS

Figure 1:
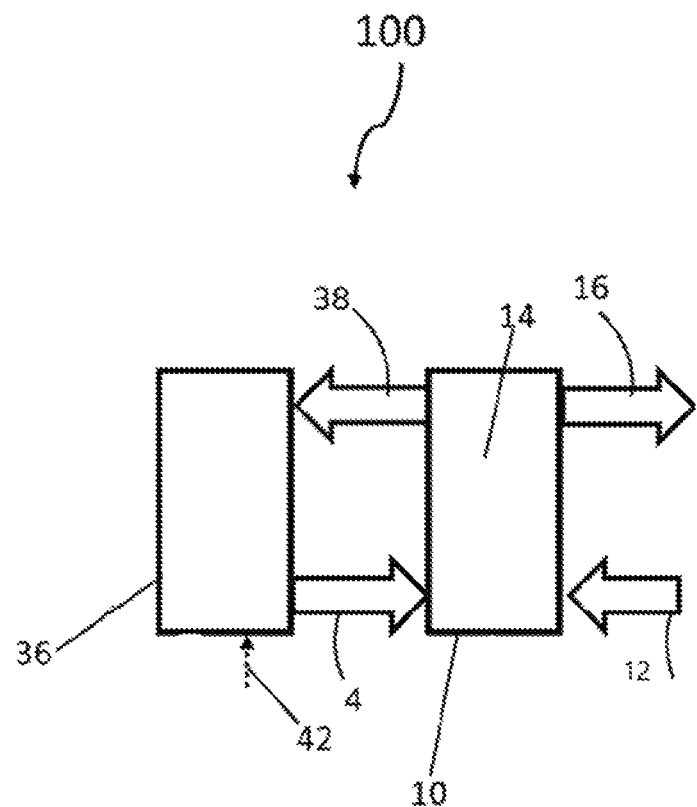
FIG. 1 shows an exemplary apparatus according to an embodiment of the invention.

As discussed briefly above, oxidative coupling of methane (OCM) and oxidative dehydrogenation (ODH) of ethane and higher hydrocarbons are reactions of significant commercial value. These conversions may be done either catalytically by feeding a hydrocarbon and an oxygen containing gas, or in a redox oxygen transfer mode whereby an Oxygen Transfer Agent (OTA) supplies the necessary oxygen for the formation of water. Either reaction (OCM or ODH) is exemplified by equation (1), and will be referred to herein as either OCM or ODH; i.e. for the purposes of this disclosure, the terms, "coupling of methane" (OCM) and "oxidative dehydrogenation" (ODH) are considered to be interchangeable.

$$zC_nH_{2n+2-2\beta} + (z-1+\delta)\text{"O"} \rightarrow C_{(z \times n)}H_{2(z \times n)+2-2\beta-2\delta} + (z-1+\delta)H_2O \quad (1)$$

where: z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen, "O" in equation (1) may be supplied by the reduction of a metal oxide or via the catalytic use of molecular oxygen. The agent that supplies the oxygen, whether a reducible metal oxide or another type of catalyst or catalyst system may be referred to herein as an oxygen transfer agent (OTA).

According to some embodiments, the oxygen transfer agent disclosed herein, when used in the oxidative dehydrogenation of a hydrocarbon feed in the presence of less than 1000 ppm weight of molecular oxygen, may undergo the following exemplary reactions:

$$CH_3CH_3 + \text{Heat} \rightarrow CH_2CH_2 + H_2$$

$$H_2 + OTA^{ox} \rightarrow H_2O + OTA^{red}$$

$$OTA^{red} + \tfrac{1}{2}O_2 \rightarrow OTA^{ox} (\text{re-oxidation})$$

Where $OTA^{ox}$ represents the oxidized form of the oxygen transfer agent disclosed herein, and $OTA^{red}$ represent the reduced form of the oxygen transfer agents disclosed herein.

A useful catalyst or oxygen transfer agent (OTA) will not only promote high conversion of the hydrocarbon feeds to high selectivities of the desired products, thereby minimizing unwanted COx and coke products, but the catalyst or oxygen transfer agent desirably has certain physical properties in order to be successfully used in these reactors.

These desirable physical properties include:

an ability to maintain fluidization at reaction temperatures; e.g. not be prone to agglomeration or excessive attrition at high temperature and thus maintain a free flowing mixture of gas and solid at reaction temperature;

good physical strength and low attrition under fluidization conditions and be able to maintain these properties over many of redox (or chemical looping) cycles;

an ability to maintain the desired reaction conversion rate and selectivity to the desired products for at least one month;

an absence of highly toxic materials, or of materials having a geometry that may cause asbestosis;

suitability for use in in a circulating fluid bed reactor; and resistance to deactivation and loss of product selectivity when exposed to common natural gas poisons such as hydrogen sulfide, carbon dioxide, water, and the like.

In addition to these desirable physical properties, the catalyst should preferably also be inexpensive to manufacture on a large scale and comparable in cost to other commercial fluid catalysts such as, for example, fluid catalytic cracking (FCC) catalysts.

The inventor has discovered a family of oxyborates that have one or more or all of these properties and are shown herein to be useful as oxygen transfer agents in OCM or ODH systems, especially in fluidized bed reactors.

These materials conform to the general empirical formulas shown in formulas (2) and (3).

$$M_3BO_5 \quad (2)$$

$$M_2'M''BO_5 \quad (3)$$

M' may be one or a combination of alkaline earth metals, actinide metals or lanthanide metals. For example, M' may be selected from Mg, Ca, Sr, Ba, and mixtures thereof. M" may be a trivalent transition metal. Non-limiting examples of M" include, but are not limited to trivalent Mn, Fe, Co, Cu, V, Nb, Ta, Cr, Mo, W, and mixtures thereof. These M" trivalent metals may comprise 100% of the metal component, or may comprises mixtures of the above metals such that the sum of the M" charge is equal to +3. Materials such as those having the formula (2) may include minerals such as those in the ludwigite class and include pinakiolite, orthopinakiolite, takeuchiite, fredrikssonite and others having an orthorhombic structure and in space group Pbam. [Cryst. Res. Technol. 52, No. 4, 1600338 (2017)] Such minerals are described by Jan-Olov Bovin, et al, Acta. Cryst. 37A ((1981) parts I-III, 28-46, the entire disclosure of which is incorporated by reference herein for all purposes. Other synthetic forms of boron, manganese and magnesia have been used as components of OCM and/or ODH catalysts or oxygen transfer agents. For example, U.S. Pat. No. 10,138, 182 B2 and EP14003879NW A1 disclose the use of $NaB_2Mn_2Mg4O_{11.5}$ and $Mg_3Mn_3B_2O_{10}$. However, these forms of oxyborates require the manganese to be present either as Mn+4 (such as in $MnO_2$) or as a mixture of Mn+2 and Mn+3 (such as in $Mn_3O_4$). The oxyborates of the present invention, and of the empirical formulas 2 and 3, have the M" metals in an average of about +3 oxidation state (such as in $Mn_2O_3$ or $Fe_2O_3$).

Oxygen Transfer Agent:

It has been found that the oxygen transfer agents of the present invention, comprising a metal-boron oxide, wherein the average oxidation state of the metal in the metal-boron oxide have an average of about +3 oxidation state, provide higher conversions and yields to the desired products when used as oxygen transfer agents or catalysts in OCM or ODH reactions than such materials having an average oxidation state such as +2 or +4. It has also been found that higher yields and selectivities are realized when the at least one oxygen transfer agent comprises 10% or less of a stoichiometric excess in moles of the at least one metal in the metal-boron oxide with respect to the boron in the oxygen transfer agent.

The inventor has further discovered that these particular oxyborates are especially effective as oxygen transfer agents or catalysts in OCM or ODH reactions when used in combination with a magnesia-phosphate cement (MPC). The magnesia-phosphate cement not only enhances the effectiveness of the metal-boron oxide as an oxygen transfer agent, but also provides enhanced physical properties to the oxygen transfer agent when used as a heterogeneous support, or binder for a heterogeneous oxygen transfer agent. Such properties include, but are not limited to: ease of processing since the magnesia-phosphate cement are quick setting with early strength onset during the cure. They also exhibit low shrinkage with little cracking during cure, and also have excellent bond characteristics to many different types of substrates. With respect to physical properties that are important when used as a heterophase oxygen transport agent in OMC and ODH reactions, these magnesia-phosphate cements have low abrasion, i.e. do not tend to damage interiors of fluidized bed reactors; high wear resistance, i.e. exhibit low attrition in such reactors; high impact resistance; and good thermal conductivity, all desirable attributes for heterophase oxygen transport agents used in fluidized bed reactors, for example. The magnesia-phosphate cements may be beneficial in imparting good attrition resistance and high thermal conductivity to the oxygen transfer agents disclosed herein.

In some embodiments, the oxygen transfer agent may comprise, consist of, or consist essentially of a compound that satisfies the formula $M_3BO_5$. M may be selected from the group consisting of alkaline earth metals, actinide metals, lanthanide metals, trivalent transition metals, and combinations thereof. According to certain embodiments, the oxygen transfer agent may comprise, consist of, or consist essentially of a compound that satisfies the formula $M'_2M''BO_5$. According to some embodiments, the metal M itself may comprise more than one type of metal, i.e. M may comprise M' and M''. M' may be selected from the group consisting of alkaline earth metals, actinide metals, lanthanide metals, and combinations thereof; and M'' may be selected from group consisting of trivalent transition metals, and combinations thereof. In some embodiments, M' may be selected from the group consisting of Mg, Ca, Sr, Ba, and mixtures thereof. In some embodiments, M'' may be selected from the group consisting of Mn, Fe, Co, Cu, V, Nb, Ta, Cr, Mo, W, and mixtures thereof. In certain embodiments, the compound that satisfies the formula $M_3BO_5$ may be selected from the ludwigite class minerals, and combinations thereof, and in some embodiments, the ludwigite class mineral may be selected from the group consisting of pinakiolite, orthopinakiolite, takeuchiite, fredrikssonite, and combinations thereof.

The inventor has discovered that the oxygen transfer agent advantageously comprises 10% by moles or less of a stoichiometric excess in moles of Mn in the oxygen transfer agent with respect to the boron in the oxygen transfer agent. Other metals that may also be limited to less than 10% by moles of a stoichiometric excess in the oxygen transfer agent with respect to the boron in the oxygen transfer agent include Fe, Co, Cu, V, Nb, Ta, Cr, Mo, or W. The inventor has discovered that minimizing a stoichiometric excess in moles of Mn, Fe, Co, Cu, V, Nb, Ta, Cr, Mo, or W with respect to the boron in the oxygen transfer agent enhances the selectivity and the yield of the ODH or OCM reactions. In particular, as will be demonstrated below, the inventors have found that the presence of $Mg_6MnO_8$ having a cubic structure and in space group of Fm3m [Acta Cryst. 7, 246 (1954)] may be detrimental to the effectiveness of the oxygen transfer agent, and that its presence can be detected in the oxygen transfer agent as a whole, by monitoring the stoichiometric excess in moles of Mn with respect to the boron, compared to what would be expected in the absence of $Mg_6MnO_8$. In particular, it has been found that 10% or less, or 9% or less, or 8% or less, or 7% or less, or 6% or less, or 5% or less, or 4% or less, or 3% or less, or 2% or less, or 1% or less of a stoichiometric excess in moles of Mn, Fe, Co, Cu, V, Nb, Ta, Cr, Mo, or W in the oxygen transfer agent with respect to the boron on the oxygen transfer agent, may be present in the oxygen transfer agent.

According to some embodiments, the at least one oxygen transfer agent may further comprise, consist of or consist essentially of, a magnesia-phosphate cement that satisfies the empirical formula: $MgM'''PO_4.mH_2O$. According to certain embodiments, M''' may be selected from the group consisting of sodium, lithium, potassium, and mixtures thereof; and m may be an integer from 0 to 6. In some embodiments, the magnesia-phosphate cement that satisfies the empirical formula $MgM'''PO_4.mH_2O$ may comprise at least one of $MgKPO_4.mH_2O$ and $MgNaPO_4.mH_2O$, and m may be an integer from 0 to 6. The integer m may be at least one of 0, 1, 2, 3, 4, 5, 6, or combinations thereof. In other words, it is possible that varying amounts of waters of hydration may be present in a single sample of the magnesia-phosphate cement. In particular embodiments, the metal-boron oxide of the oxygen transfer agent may comprise, consist of, or consist essentially of $Mg_2MnO_2(BO_3)$ and the magnesia-phosphate cement may comprise, consist of, or consist essentially of $NaMg(PO_4).mH_2O$.

In other embodiments, the at least one oxygen transfer agent may further comprise at least one promotor selected from the group consisting of alkali metals, such as Na, Li and K; alkaline earth metals such as Ca, Sr and Ba, and mixtures thereof. The at least one promoter may be selected from the group consisting of $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, $CaSO_4$, $Na_2SO_4$, $NaHSO_4$, and mixtures thereof.

Methods of Oxidatively Dehydrogenating a Hydrocarbon Feed to Produce a Dehydrogenated Hydrocarbon Product and Water:

A method of oxidatively dehydrogenating a hydrocarbon feed is carried out by contacting the feed with an oxidation transfer agent may proceed in the substantial absence of molecular oxygen or in the presence of molecular oxygen. In the former case, the oxidation transfer agent as disclosed herein may itself provide the necessary oxygen, and thus may convert to a reduced form. In a separate step, this reduced form may be re-oxidized in the presence of molecular oxygen. In the latter case, the oxidation transfer agent as disclosed herein may be acting more like a catalyst, i.e., not necessarily being changed after the oxidative dehydrogenation of the hydrocarbon feed is complete.

A method of oxidatively dehydrogenating a hydrocarbon feed to produce a dehydrogenated hydrocarbon product and water is provided. The method comprises, consists of, or consists essentially of the steps of:

a) Contacting the hydrocarbon feed with at least one oxygen transfer agent comprising a metal-boron oxide. The average oxidation state of the metal in the metal-boron oxide is from 2.7+ to less than 4.0+, and the at least one oxygen transfer agent comprises, consists of, or consists essentially of 10% or less of a stoichiometric excess in moles of Mn with respect to the boron in the oxygen transfer agent; and b) Oxidatively dehydrogenating the hydrocarbon feed at reaction conditions to produce the dehydrogenated hydrocarbon product and the water.

According to some embodiments, the reaction conditions in step b) comprise, consist of, or consist essentially of the presence of essentially no molecular oxygen during the oxidative dehydrogenation of the hydrocarbon feed. In this embodiment, at least a portion of the oxygen transfer agent may be reduced to produce a reduced oxygen transfer agent. Without wishing to be bound by theory, this condition means that the oxygen needed for the oxidative dehydrogenation may be supplied by the at least one oxygen transfer agent. In particular, less than 5 wt %, less than 4 wt %, less than 3 wt %, less than 2 wt %, less than 1 wt %, less than 0.5 wt %, less than 1000 ppm weight, less than 500 ppm weight of molecular oxygen with respect to the total amount of the hydrocarbon feed, the oxygen transfer agent and the molecular oxygen is present during the oxidative dehydrogenation step. Less than 1000 ppm weight of molecular oxygen is preferred. Non-limiting examples of sources of molecular oxygen are air, or molecular oxygen-containing streams resulting from other chemical processes.

According to some embodiments the reaction conditions in step b) may comprise temperatures of from 825-840° C. and at gas hourly space velocities of 2,400 to 4,800 hr$^{-1}$. Other suitable temperatures may be from 300° C. to 1000° C., 350° C. to 1000° C., 400° C. to 1000° C., 400° C. to 800° C., or from 500° C. to 700° C. Pressure may be from sub-atmospheric to super-atmospheric with a range of 0.1 to 100 atm. In other embodiments, the pressure range may be 0.9 to 10 atm. Other pressure ranges may be from 0.9 to 1.5, 0.5 to 2, 0.9 to 5, 0.9 to 7, or 0.9 to 1.1 atm. 600-950° C., or from 500-900° C. or from 700-900° C. or from 800-850° C.

According to other embodiments, the reaction conditions in step b) may comprise, consist of, or consist essentially of providing a source of molecular oxygen in an amount of greater than 1000 ppm weight of molecular oxygen during the oxidative dehydrogenation of the hydrocarbon feed. Without wishing to be bound by theory, this condition means that the oxygen needed for the oxidative dehydrogenation of the hydrocarbon feed is supplied by the source of molecular oxygen. Accordingly, again without being bound by theory, the at least one oxygen transfer agent may be acting as a catalyst in the reaction, i.e., facilitating the oxidative dehydrogenation of the hydrocarbon feed by the source of molecular oxygen, rather than supplying the oxygen itself. According to some embodiments, more than 1000 pp weight, 2000 ppm weight, 3000 ppm weight, 0.5 wt %, more than 1 wt %, more than 5 wt %, more than 10 wt %, more than 20 wt % of molecular oxygen with respect to the total amount of the hydrocarbon feed, the oxygen transfer agent and the molecular oxygen may be supplied to the oxidative dehydrogenation step. According to some embodiments, in addition to providing the source of molecular oxygen, the reaction conditions may further comprise, consist of, or consist essentially of that the oxygen transfer agent comprises less than 5 wt %, or less than 4 wt % or less than 3 wt % or less than 2 wt % or less than 1%, or none, of a perovskite, by weight of the oxygen transfer agent. In embodiments where a source of oxygen is present during the oxidative dehydrogenation step, the oxygen transfer agent may have a form that has an aspect ratio of less than 10, or less than 9, or less than 8, or less than 7, or less than 6, or less than 5, or less than 5, or less than 4, or less than 3, or less than 2.

According to some embodiments, the step b) oxidatively dehydrogenating the hydrocarbon feed of the method may proceed according to the reaction:

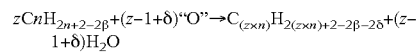

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the at least one oxygen transfer agent. According to some embodiments, z=2, n=1, β=0, and δ=0. In particular this means that the reaction may comprise the oxidative coupling of methane to form ethylene. According to other embodiments, z=1, n=2, β=0, and δ=1. In particular, this means that the reaction may comprise the oxidative dehydrogenation of ethane to form ethylene. The oxidative dehydrogenation may comprise more than one reaction. Non-limiting examples of such multiple reactions may include: skeletal isomerization of olefins; oxidative dehydrogenation of methane to ethane and ethylene, and oxidative dehydrogenation of ethane to ethylene and higher olefins such as propylene and butylene.

According to some embodiments the method may further comprise, consist of or consist essentially of a step c) of contacting the at least one oxygen transfer agent with a gas-phase promoter selected from the group consisting of gas phase water; steam; $CO_2$; halide gases; hydrogen halides such as HCl, HBr, and HF; sulfur containing gases such as hydrogen sulfide, oxides of sulfur, and organo-sulfur compounds; and mixtures thereof. According to particular embodiments, the step c) may be performed at the same time as the step a).

According to some embodiments, the method of oxidatively dehydrogenating a hydrocarbon feed may further comprise, consist of, or consist essentially of steps d) removing a portion of the reduced oxygen transfer agent; e) contacting the portion of the oxygen transfer agent with a gas comprising molecular oxygen to produce a regenerated oxygen transfer agent; and f) feeding the regenerated oxygen transfer agent to the step a).

The oxygen transfer agents according to various embodiments of the present invention may be used in a chemical looping system to promote an ODH reaction via a Mars-van Krevelen-like mechanism. The effective utilization of the chemical looping mode of this invention may be performed in either fixed or circulating bed reactors. In the case of fixed bed reactors, multiple reactors may be used such that the oxidative dehydrogenation of the hydrocarbon feed and the re-oxidation of the oxygen transfer agent are occurring continuously and in parallel as the hydrocarbon feed and the source of molecular oxygen (such as air) are alternately cycled between the reactor and a regeneration unit while the re-oxidation takes place.

Apparatus for Producing a Dehydrogenated Hydrocarbon Product:

FIG. 1 shows a schematic of an apparatus 100 for producing a dehydrogenated hydrocarbon product in stream 16 by oxidative dehydrogenation of a hydrocarbon feed in stream 12 to produce the dehydrogenated hydrocarbon product and water. The apparatus 100 comprises, consists of or consists essentially of:

a vessel 10 configured and arranged for:
 i) contacting the hydrocarbon feed 12 with the at least one oxygen transfer agent 14 disclosed herein; and
 ii) oxidatively dehydrogenating the hydrocarbon feed 12 at reaction conditions to produce the dehydrogenated hydrocarbon product and the water in stream 16 and to convert a portion of the oxygen transfer agent 14 to a reduced oxygen transfer agent 38, wherein the reaction conditions comprise less than 1000 ppm weight of molecular oxygen with respect to the total amount of hydrocarbon feed 12, the oxygen transfer agent 14 and the molecular oxygen.

According to some embodiments, the vessel 14 may be a reactor selected from a fluidized bed reactor, a moving bed reactor, or a shell and tube reactor. The vessel may further comprise an inlet and an outlet. The apparatus 100 may further comprise a regeneration unit 36 in communication with the inlet and the outlet. The regeneration unit may be constructed and arranged to:

iii) receive the reduced oxygen transfer agent 38 from the outlet;
 iv) contact the reduced oxygen transfer agent 38 with a gas comprising molecular oxygen 42 to produce a regenerated oxygen transfer agent 4; and
 v) feed the regenerated oxygen transfer agent 38 to the inlet.

In the instance where the conversions of (1) are run in a co-feed mode with a mixture of hydrocarbon feed 12 and the oxygen transfer agent 38 are fed the vessel 14 together, it will be useful to use reactors as vessel 14 that can effectively remove the heat of reaction, such as shell and tube reactors.

The oxygen transfer agents according to various embodiments of the present invention may be used in a chemical looping system to promote an ODH reaction via a Mars-van Krevelen-like mechanism. The effective utilization of the chemical looping mode of this invention may be performed in either fixed or circulating bed reactors. In the case of fixed bed reactors, multiple reactors 14 and regeneration units 36 may be used such that hydrocarbon oxidation and the re-oxidation of the oxygen transfer agent are occurring continuously as hydrocarbon feed 12 and the source of molecular oxygen 42, which may be or comprise air are alternately cycled to multiple reactors.

Hydrocarbon Feed:

Suitable hydrocarbon feeds for use in embodiments of the present invention may be selected from methane; ethane; propane; isomers of butane; isomers of butene, isomers of pentane; isomers of pentene; isomers of hexane; cyclohexane; isomers of hexene; cyclohexene; and mixtures thereof.

Aspects of the invention may be summarized as follows:

Aspect 1: A method of oxidatively dehydrogenating a hydrocarbon feed to produce a dehydrogenated hydrocarbon product and water, the method comprising:
 a) contacting the hydrocarbon feed with at least one oxygen transfer agent comprising a metal-boron oxide, wherein the average oxidation state of the metal in the metal-boron oxide is from 2.7+ to less than 4.0+, and the at least one oxygen transfer agent comprises 10% or less of a stoichiometric excess in moles of Mn with respect to the boron; and
 b) oxidatively dehydrogenating the hydrocarbon feed at reaction conditions to produce the dehydrogenated hydrocarbon product and the water.

Aspect 2: The method according to Aspect 1, wherein the reaction conditions comprise less than 1000 ppm weight of molecular oxygen with respect to the total amount of the hydrocarbon feed, the oxygen transfer agent and the molecular oxygen, and wherein at least a portion of the oxygen transfer agent is reduced to produce a reduced oxygen transfer agent.

Aspect 3: The method according to either Aspect 1 or Aspect 2, wherein the reaction conditions comprise providing a source of molecular oxygen in an amount greater than 1000 ppm weight.

Aspect 4: The method according to any of Aspects 1-3, wherein the at least one oxygen transfer agent has a shape characterized by an aspect ratio of less than 10.

Aspect 5: The method according to any of Aspects 1-4, wherein the at least one oxygen transfer agent comprises a compound that satisfies the formula $M_3BO_5$, wherein M is selected from the group consisting of alkaline earth metals, actinide metals, lanthanide metals, trivalent transition metals, and combinations thereof.

Aspect 6: The method according to any of Aspects 1-5, wherein the at least one oxygen transfer agent comprises a compound that satisfies the formula $M'_2M''BO_5$, wherein M' is selected from the group consisting of alkaline earth metals, actinide metals, lanthanide metals, and combinations thereof; and M'' is selected from group consisting of trivalent transition metals, and combinations thereof.

Aspect 7: The method according to Aspect 6, wherein M' is selected from the group consisting of Mg, Ca, Sr, Ba, and mixtures thereof.

Aspect 8: The method according to either Aspect 6 or Aspect 7, wherein M'' is selected from the group consisting of Mn, Fe, Co, Cu, V, Nb, Ta, Cr, Mo, W, and mixtures thereof.

Aspect 9: The method according to any of Aspects 5-8, wherein the compound that satisfies the formula $M_3BO_5$ is selected from the ludwigite class minerals, and combinations thereof.

Aspect 10: The method according to Aspect 9, wherein the ludwigite class mineral is selected from the group consisting of pinakiolite, orthopinakiolite, takeuchiite, fredrikssonite, and combinations thereof.

Aspect 11: The method according to any of Aspects 1-10, wherein the at least one oxygen transfer agent further comprises a magnesia-phosphate cement that satisfies the formula:

wherein M''' is selected from the group consisting of sodium, lithium, potassium, and mixtures thereof; and m is an integer from 0 to 6.

Aspect 12: The method according to Aspect 11, wherein the magnesia-phosphate cement comprises at least one of $MgKPO_4.mH_2O$ and $MgNaPO_4.mH_2O$, wherein m is an integer from 0 to 6.

Aspect 13: The method according to either Aspect 11 or Aspect 12, wherein the metal-boron oxide comprises $Mg_2MnO_2(BO_3)$ and the magnesia-phosphate cement comprises $NaMg(PO_4).mH_2O$.

Aspect 14: The method according to any of Aspects 1-13, wherein the at least one oxygen transfer agent further comprises at least one promotor selected from the group consisting of alkali metals, alkaline earth metals, and mixtures thereof.

Aspect 15: The method according to Aspect 14, wherein the at least one promoter is selected from the group consisting of $Li_2WO_4$, $Na_2WO_4$, $K_2WO_4$, $SrWO_4$, $Li_2MoO_4$, Na$_2$MoO$_4$, K$_2$MoO$_4$, CsMoO$_4$, Li$_2$CO$_3$, Na$_2$CO$_3$, K$_2$CO$_3$, CaSO$_4$, Na$_2$SO$_4$, NaHSO$_4$, and mixtures thereof.

Aspect 16: The method according to any of Aspects 1-15, wherein the step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen.

Aspect 17: The method according to any of Aspects 2-15, wherein the step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the at least one oxygen transfer agent.

Aspect 18: The method according to any of Aspects 3-15, wherein the step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the source of molecular oxygen.

Aspect 19: The method according to any of Aspects 16-18, wherein z=2, n=1, β=0, and δ=0.

Aspect 20: The method according to any of Aspects 16-18, wherein z=1, n=2, β=0, and δ=1.

Aspect 21: The method according any of Aspects 1-20, further comprising a step c) of contacting the at least one oxygen transfer agent with a gas-phase promoter.

Aspect 22: The method according Aspect 21, wherein the gas-phase promoter is selected from the group consisting of gas phase water, steam, CO$_2$, halide gases, hydrogen halides, sulfur containing gases, and mixtures thereof.

Aspect 23: The method according to either Aspect 21 or Aspect 22, wherein the step c) is performed at the same time as the step a).

Aspect 24: The method according to any of Aspects 2-23, further comprising:
d) removing a portion of the reduced oxygen transfer agent;
e) contacting the portion of the reduced oxygen transfer agent with a gas comprising molecular oxygen to produce a regenerated oxygen transfer agent; and
f) feeding the regenerated oxygen transfer agent to step a).

Aspect 25: An apparatus for producing a dehydrogenated hydrocarbon product by oxidative dehydrogenation of a hydrocarbon feed to produce the dehydrogenated hydrocarbon product and water, the apparatus comprising:
at least one vessel configured and arranged for:
i) contacting the hydrocarbon feed with at least one oxygen transfer agent comprising a metal-boron oxide, wherein the average oxidation state of the metal is from 2.7+ to less than 4.0+, and the at least one oxygen transfer agent comprises 10% or less of a stoichiometric excess in moles of Mn with respect to the boron; and
ii) oxidatively dehydrogenating the hydrocarbon feed at reaction conditions to produce the dehydrogenated hydrocarbon product and the water and to convert a portion of the oxygen transfer agent to a reduced oxygen transfer agent, wherein the reaction conditions comprise less than 1000 ppm weight of molecular oxygen with respect to the total amount of hydrocarbon feed, the oxygen transfer agent and the molecular oxygen.

Aspect 26: The apparatus according to Aspect 25, wherein the at least one vessel is selected from a fluidized bed reactor, a moving bed reactor, or a shell and tube reactor.

Aspect 27: The apparatus according to either Aspect 25 or Aspect 26, wherein the at least one vessel comprises an inlet and an outlet, and wherein the apparatus further comprises a regeneration unit in communication with the inlet and the outlet, wherein the regeneration unit is constructed and arranged to:
iii) receive at least a portion of the reduced oxygen transfer agent from the outlet;
iv) contact the at least a portion of the reduced oxygen transfer agent with a gas comprising molecular oxygen to produce a regenerated oxygen transfer agent; and
v) feed the regenerated oxygen transfer agent to the inlet.

Aspect 28: An oxygen transfer agent comprising:
a metal-boron oxide;
a magnesia-phosphate cement;
and 5% by weight or less of Mg$_6$MnO$_8$;
wherein:
the average oxidation state of the metal in the metal-boron oxide is from 2.7+ to less than 4.0+, and the at least one oxygen transfer agent comprises 10% or less of a stoichiometric excess of Mn with respect to the boron; and the magnesia-phosphate cement comprises: MgM'''PO$_4$.mH$_2$O, wherein m is an integer from 0 to 6.

Aspect 29: The oxygen transfer agent according to Aspect 28, wherein the metal-boron oxide comprises a compound that satisfies the formula M$_3$BO$_5$;
wherein M is selected from the group consisting of alkaline earth metals, actinide metals, lanthanide metals, trivalent transition metals, and combinations thereof.

Aspect 30: The oxygen transfer agent according to either Aspect 28 or Aspect 29, wherein the metal-boron oxide comprises a compound that satisfies the formula M'$_2$M"BO$_5$,
wherein M' is selected from the group consisting of alkaline earth metals, actinide metals, lanthanide metals, and combinations thereof; and M" is selected from group consisting of trivalent transition metals, and combinations thereof.

Aspect 31. The oxygen transfer agent according to Aspect 30, wherein M' is selected from the group consisting of Mg, Ca, Sr, Ba, and mixtures thereof and M" is selected from the group consisting of Mn, Fe, Co, Cu, V, Nb, Ta, Cr, Mo, W, and mixtures thereof.

Aspect 32. The oxygen transfer agent according to any of Aspects 28-31, wherein M''' is selected from the group consisting of sodium, lithium, potassium, and mixtures thereof.

Aspect 33. The oxygen transfer agent according to any of Aspects 29-32, wherein the compound that satisfies the formula $M_3BO_5$ is selected from the ludwigite class minerals, and combinations thereof.

Aspect 34. The oxygen transfer agent according to any of Aspects 28-33, further comprising a promotor selected from the group consisting of group consisting of alkali metals, alkaline earth metals, and mixtures thereof.

Aspect 35. The oxygen transfer agent according to Aspect 34, wherein the at least one promoter is selected from the group consisting of $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, $CaSO_4$, $Na_2SO_4$, $NaHSO_4$, and mixtures thereof.

EXAMPLES

The following non-limiting examples are provided for the purpose of elucidating the advantages obtained from aspects of the present invention and are not intended to limit the invention to only these exemplary embodiments.

Example 1: (Oxygen Transfer Agent with Magnesia-Phosphate Cement)

As an example, a manganese-boron catalyst was made in the presence of a sodium magnesium phosphate cement by the following procedure. MgO (16.72 g), $MnO_2$ (12.88 g), $H_3BO_3$ (4.58 g) and $Na_4P_2O_7$ (14.77 g) where dry mixed. To this mixture was added a sodium silicate solution of Ludox 30 (8.58 g) and enough additional distilled water to make a plaster like paste. This mixture was allowed to air dry for 12 hours at 110 C. After drying, the mixture had formed a hard brick like cake. This cake was then calcined at 900° C. in air for 12 hours. The resulting material was hammered and broken down to 14 by 30 mesh particles, such that the average particle size had an aspect ratio of approximately 2. The particles had a tapped density of 1.35 g/cc. The primary active manganese species was identify by XRD as $Mg_2MnO_2(BO_3)$ (fredrikssonite). Also identified by XRD was the magnesia-phosphate cement material $NaMg(PO_4)$. Importantly, XRD showed no formation of $Mg_6MnO_8$ and therefore the oxygen transfer agent had no stoichiometric excess in moles of Mn with respect to the boron. Upon reduction of this catalyst, either by hydrogen or reaction with ethane, the fredrikssonite phase disappeared, but re-appeared upon treatment with air at 825-950° C. No perovskite was detected.

Example 2: (Comparative Oxygen Transfer Agent not Conforming to $M_3BO_5$ or $M'_2M''BO_5$)

In this example, the oxygen transfer agent was made by dry mixing MgO (16.72 g), $MnO_2$ (12.88 g), $H_3BO_3$ (4.58 g) and LiOH (1.78 g). To this mixture was added a sodium silicate solution of Ludox 30 (8.58 g) and enough additional distilled water to make a paste. This mixture was allowed to air dry for 12 hours at 110° C. After drying, the mixture had formed a soft cake. This cake was then calcined at 900° C. in air for 12 hours. The resulting material was hammered and broken down to 14 by 30 mesh particles (i.e., the aspect ratio of the particles was approximately 2) and had a tapped density of 0.86 g/cc. The primary manganese compounds identified by XRD were $Mg_6MnO_8$ and $NaMnO_4$, i.e., the oxygen transfer agent in this comparative example did not contain a material conforming to either $M_3BO_5$ or $M'_2M''BO_5$. No manganese metal borates were detected. The boron was observed as $Mg_3(BO_3)_2$ (kotoite). This is not an oxygen transfer agent, since there are no reducible elements in this material capable of being reduced at the reaction conditions utilized in the present application. In other words, Mg+2 would not be reduced to Mg+1 or Mg), and B+3 also would not be reduced.

Figure 2:
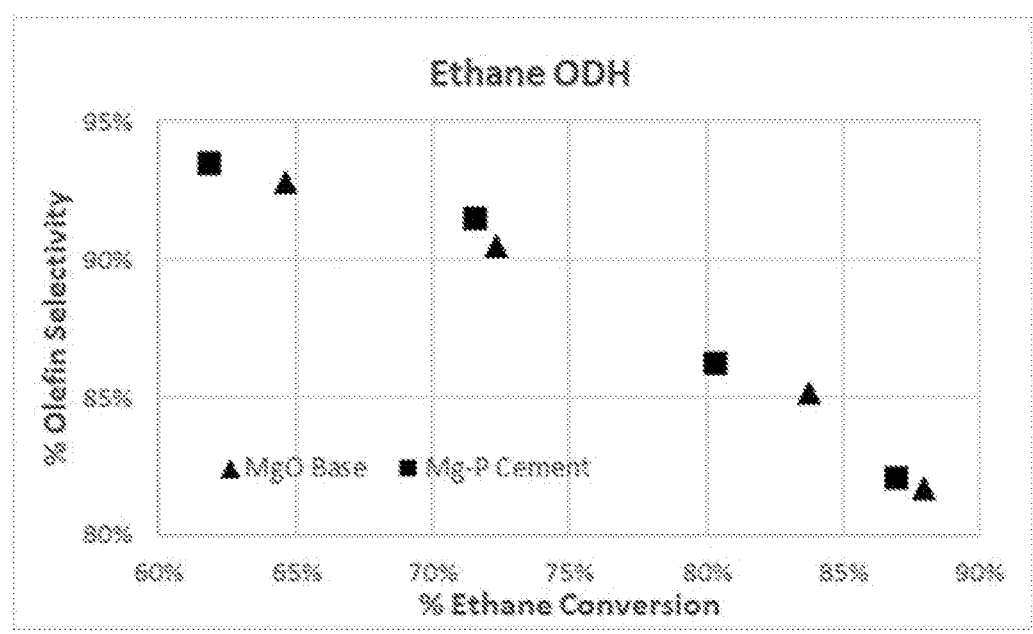
FIG. 2 shows the conversion of ethane vs. the selectivity to the desired ethylene and heavier olefins as a function of the reaction conversion for the oxygen transfer agents of Example 1 (designated as Mg—P cement) Example 2 (designated as MgO)
Figure 3:
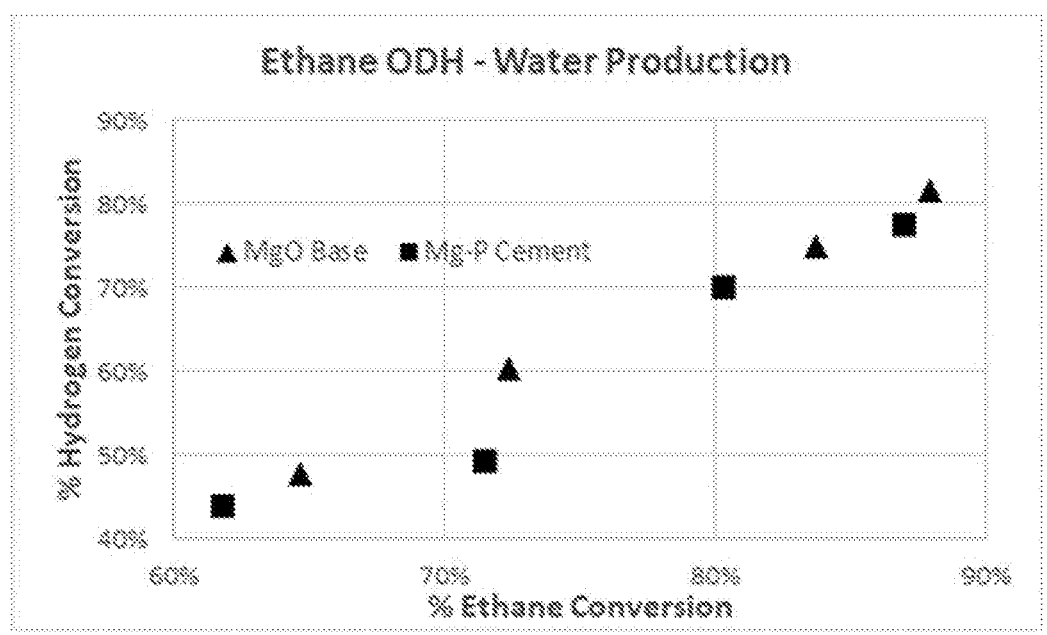
FIG. 3 shows the conversion of ethane vs. the ability of the OTA to convert in-situ generated hydrogen to water for the oxygen transfer agents of Example 1 (designated as Mg—P cement) and Example 2 (designated as MgO).

Example 1 (OTA conforming to $M_3BO_5$ or $M'_2M''BO_5$) and Comparative Example 2 (OTA not conforming to $M_3BO_5$ or $M'_2M''BO_5$) were evaluated for oxidative dehydrogenation of ethane at 825-840° C. and at gas hourly space velocities of 2,400 to 4,800 $hr^{-1}$. The conversions were done in a cyclic redox mode such that ethane and air, or oxygen, were not present at the same time in the reactor. Nitrogen was used to purge after a 15 second pulse of ethane, and after a 10 minute regeneration of the reduced OTA. Products were collected with gas bags and analyzed by gas chromatography. Samples of the spent air from regeneration of the OTA showed minimal carbon oxide formation, and therefore indicate that very there was very little coke formation during the ethane cycle. The results from these experiments are shown in FIGS. 1 and 2. The oxygen transfer agent that further comprised the magnesium phosphate cement had very similar activity and selectivity to ethylene and olefins as the made without the magnesia-phosphate cement. The conversion of in-situ hydrogen, or water selectivity, were also comparable between the two systems.

The two oxygen transfer agents of Example 1 and comparative Example 2 were also evaluated in an up-flowing fluidized bed of particles with approximately a 70 micron average diameter. The ethane ODH results between the two oxygen transfer agents were identical, however the comparative oxygen transfer agents that did not conform to $M_3BO_5$ or $M'_2M''BO_5$ made without the magnesium phosphate cement defluidized above 825° C.

The key differences observed between the oxygen transfer agent of Example 1 and oxygen transfer agent of Example 2 were:

- The Example 1 oxygen transfer agent that comprised the MPC and conformed to $M_3BO_5$ or $M'_2M''BO_5$ had significantly higher density than the Example 2 oxygen transfer agent which should trend towards much higher attrition resistance in a fluidized bed reactor.
- The Example 2 OTA started to defluidize at temperatures above 825° C. The Example 2 OTA was observed to be fused together after cooling down the reactor and discharged.
- No defluidization of the Example 1 OTA occurred at temperatures up to at least 1,000° C. After 1,500 cycles of the Example 1 OTA, the oxygen transfer agent flowed freely from the reactor after cooling down the reactor and discharging the oxygen transfer agent.

Example 3

Manganese (II) acetate tetrahydrate (20 g), Magnesium (II) tetrahydrate (35 g) and boric acid (5 g) in a mole ratio of 1:2:1 of Mn:Mg:B were intimately dry mixed. To the resulting powder was added 60 ml of water and the mixture brought to 60° C. which allowed dissolution of all components. The water from this solution was removed by drying for 16 hours at 110° C. The resulting dry powder was calcined at 900° C. for 16 hours. X-ray diffraction (XRD) analysis of the resulting brown powder indicated the formation of fredrikssonite, $Mg_2Mn(BO_5)$. A 5 g sample of fredrikssonite was subjected to a flow of hydrogen gas at 850° C. The total hydrogen volume was over 10 times the molar equivalent required to reduce Mn (III) to Mn (II). Water was observed as a product. XRD of the resulting pale green reduced powder indicated a total loss of fredrikssonite, i.e. the fredrikssonite was able to transfer its oxygen to hydrogen to produce water. This experiment demonstrates that materials in the family of $Mg_2Mn(BO_5)$ (i.e., conforming to $M_3BO_5$ or $M'_2M''BO_5$) are useful as oxygen transfer agents for the reaction of the hydrogen formed when ethane and other hydrocarbons are pyrolyzed to olefins.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the invention. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method of oxidatively dehydrogenating a hydrocarbon feed to produce a dehydrogenated hydrocarbon product and water, the method comprising:
   a) contacting the hydrocarbon feed with at least one oxygen transfer agent comprising a metal-boron oxide, wherein the average oxidation state of the metal in the metal-boron oxide is from 2.7+ to less than 4.0+, and the at least one oxygen transfer agent comprises 10% or less of a stoichiometric excess in moles of Mn with respect to the boron; and
   b) oxidatively dehydrogenating the hydrocarbon feed at reaction conditions to produce the dehydrogenated hydrocarbon product and the water,
   wherein the at least one oxygen transfer agent is selected from the group consisting of a compound that satisfies the formula $M_3BO_5$, a compound that satisfies the formula $M'_2M''BO_5$, and mixtures thereof; and
   wherein M is selected from the group consisting of alkaline earth metals, actinide metals, lanthanide metals, trivalent transition metals, and combinations thereof; M' is selected from the group consisting of alkaline earth metals, actinide metals, lanthanide metals, and combinations thereof; and M'' is selected from group consisting of trivalent transition metals, and combinations thereof.

2. The method according to claim 1, wherein the reaction conditions comprise less than 1000 ppm weight of molecular oxygen with respect to the total amount of the hydrocarbon feed, the oxygen transfer agent and the molecular oxygen, and wherein at least a portion of the oxygen transfer agent is reduced to produce a reduced oxygen transfer agent.

3. The method according to claim 2, wherein the step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

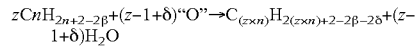

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the at least one oxygen transfer agent.

4. The method according to claim 2, further comprising:
   d) removing a portion of the reduced oxygen transfer agent;
   e) contacting the portion of the reduced oxygen transfer agent with a gas comprising molecular oxygen to produce a regenerated oxygen transfer agent; and
   f) feeding the regenerated oxygen transfer agent to step a).

5. The method according to claim 1, wherein the reaction conditions comprise providing a source of molecular oxygen in an amount greater than 1000 ppm weight.

6. The method according to claim 5, wherein
   the at least one oxygen transfer agent has a shape characterized by an aspect ratio of less than 10.

7. The method according to claim 5, wherein the step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

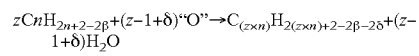

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the source of molecular oxygen.

8. The method according to claim 1, wherein M' is selected from the group consisting of Mg, Ca, Sr, Ba, and mixtures thereof.

9. The method according to claim 1, wherein M'' is selected from the group consisting of Mn, Fe, Co, Cu, V, Nb, Ta, Cr, Mo, W, and mixtures thereof.

10. The method according to claim 1, wherein the compound that satisfies the formula $M_3BO_5$ is selected from the ludwigite class minerals, and combinations thereof.

11. The method according to claim 10, wherein the ludwigite class mineral is selected from the group consisting of pinakiolite, orthopinakiolite, takeuchiite, fredrikssonite, and combinations thereof.

12. The method according to claim 1, wherein the at least one oxygen transfer agent further comprises a magnesia-phosphate cement that satisfies the formula:

$$MgM'''PO_4 \cdot mH_2O;$$

wherein M''' is selected from the group consisting of sodium, lithium, potassium, and mixtures thereof; and m is an integer from 0 to 6.

13. The method according to claim 12, wherein the magnesia-phosphate cement comprises at least one of $MgKPO_4 \cdot mH_2O$ and $MgNaPO_4 \cdot mH_2O$, wherein m is an integer from 0 to 6.

14. The method according to claim 13, wherein the metal-boron oxide comprises $Mg_2MnO_2(BO_3)$ and the magnesia-phosphate cement comprises $NaMg(PO_4) \cdot mH_2O$.

15. The method according to claim 1, wherein the at least one oxygen transfer agent further comprises at least one promotor selected from the group consisting of alkali metals, alkaline earth metals, and mixtures thereof.

16. The method according to claim 15, wherein the at least one promoter is selected from the group consisting of $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, $CaSO_4$, $Na_2SO_4$, $NaHSO_4$, and mixtures thereof.

17. The method according to claim 1, wherein the step b) oxidatively dehydrogenating the hydrocarbon feed proceeds according to the reaction:

$$zCnH_{2n+2-2\beta}+(z-1+\delta)\text{"O"} \rightarrow C_{(z \times n)}H_{2(z \times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen.

18. The method according to claim 17, wherein z=2, n=1, β=0, and δ=0.

19. The method according to claim 17, wherein z=1, n=2, β=0, and δ=1.

20. The method according claim 1, further comprising a step c) of contacting the at least one oxygen transfer agent with a gas-phase promoter.

21. The method according claim 20, wherein the gas-phase promoter is selected from the group consisting of gas phase water, steam, $CO_2$, halide gases, hydrogen halides, sulfur containing gases, and mixtures thereof.

22. The method according to claim 20, wherein the step c) is performed at the same time as the step a).

23. A method of oxidatively dehydrogenating a hydrocarbon feed to produce a dehydrogenated hydrocarbon product and water, the method comprising:
a) contacting the hydrocarbon feed with at least one oxygen transfer agent comprising a metal-boron oxide, wherein the average oxidation state of the metal in the metal-boron oxide is from 2.7+ to less than 4.0+, and the at least one oxygen transfer agent comprises 10% or less of a stoichiometric excess in moles of Mn with respect to the boron; and
b) oxidatively dehydrogenating the hydrocarbon feed at reaction conditions to produce the dehydrogenated hydrocarbon product and the water,
wherein the at least one oxygen transfer agent further comprises a magnesia-phosphate cement that satisfies the formula:

$$MgM'''PO_4 \cdot mH_2O;$$

wherein M''' is selected from the group consisting of sodium, lithium, potassium, and mixtures thereof; and m is an integer from 0 to 6.

24. The method according to claim 23, wherein the at least one oxygen transfer agent comprises a compound that satisfies the formula $M_3BO_5$,
wherein M is selected from the group consisting of alkaline earth metals, actinide metals, lanthanide metals, trivalent transition metals, and combinations thereof.

25. The method according to claim 23, wherein the at least one oxygen transfer agent comprises a compound that satisfies the formula $M'_2M''BO_5$,
wherein M' is selected from the group consisting of alkaline earth metals, actinide metals, lanthanide metals, and combinations thereof; and M'' is selected from group consisting of trivalent transition metals, and combinations thereof.

26. The method according to claim 23, wherein the magnesia-phosphate cement comprises at least one of $MgKPO_4 \cdot mH_2O$ and $MgNaPO_4 \cdot mH_2O$, wherein m is an integer from 0 to 6.

27. The method according to claim 26, wherein the metal-boron oxide comprises $Mg_2MnO_2(BO_3)$ and the magnesia-phosphate cement comprises $NaMg(PO_4) \cdot mH_2O$.

* * * * *